United States Patent
Rana et al.

(10) Patent No.: US 10,183,237 B2
(45) Date of Patent: Jan. 22, 2019

(54) METHOD AND APPARATUS FOR THE EQUILIBRATION OF A PACKED CHROMATOGRAPHY COLUMN

(71) Applicant: BIOTAGE AB, Uppsala (SE)

(72) Inventors: Sunil Rana, Mid Glamorgan (GB); Steve Jordan, Herts (GB); Geoff Davies, Gwent (GB)

(73) Assignee: BIOTAGE AB, Uppsala (SE)

( * ) Notice: Subject to any disclaimer, the term of this patent is extended or adjusted under 35 U.S.C. 154(b) by 135 days.

(21) Appl. No.: 15/127,649

(22) PCT Filed: Mar. 20, 2015

(86) PCT No.: PCT/EP2015/055997
§ 371 (c)(1),
(2) Date: Sep. 20, 2016

(87) PCT Pub. No.: WO2015/140326
PCT Pub. Date: Sep. 24, 2015

(65) Prior Publication Data
US 2017/0050120 A1    Feb. 23, 2017

(30) Foreign Application Priority Data
Mar. 21, 2014 (SE) ..................... 1450333

(51) Int. Cl.
*B01D 15/20* (2006.01)
*B01D 15/16* (2006.01)
(Continued)

(52) U.S. Cl.
CPC ......... *B01D 15/203* (2013.01); *B01D 15/165* (2013.01); *B01D 15/166* (2013.01);
(Continued)

(58) Field of Classification Search
CPC .. B01D 15/203; B01D 15/165; B01D 15/166; G01N 30/34; G01N 2030/347; G01N 30/54
See application file for complete search history.

(56) References Cited

U.S. PATENT DOCUMENTS 4,591,442 A * 5/1986 Andrews .............. B01D 15/165
                                                           210/198.2
4,942,018 A    7/1990 Munk
(Continued)

FOREIGN PATENT DOCUMENTS

| WO | 99/19514 A1 | 4/1999 |
| WO | 01/66128 A1 | 9/2001 |
| WO | 01/80965 A1 | 11/2001 |

OTHER PUBLICATIONS

International Search Report, dated Jul. 2, 2015, from corresponding PCT application.

*Primary Examiner* — Paul West
(74) *Attorney, Agent, or Firm* — Young & Thompson

(57) ABSTRACT

Disclosed is a method for equilibrating a chromatography column including the steps of (i) providing a mobile phase; and (ii) passing the mobile phase through a packed chromatography column; wherein the mobile phase includes two liquids, the proportions of which change as it is passed through the column. Also discussed are automated aspects of the method, as well as a system capable of performing such method.

14 Claims, 4 Drawing Sheets

Isocratic equilibration at a default flow rate of 25ml/min

(51) Int. Cl.
*G01N 30/36* (2006.01)
*G01N 30/54* (2006.01)
*G01N 30/72* (2006.01)
*G01N 30/34* (2006.01)

(52) U.S. Cl.
CPC ............. *G01N 30/34* (2013.01); *G01N 30/36* (2013.01); *G01N 30/54* (2013.01); *G01N 30/7233* (2013.01); *G01N 2030/347* (2013.01)

(56) References Cited

U.S. PATENT DOCUMENTS

2011/0089033 A1* 4/2011 Shimaoka ............ B01D 15/322
                                                  204/451
2013/0267510 A1* 10/2013 Alvaro ................. C07D 405/12
                                                  514/230.5

\* cited by examiner

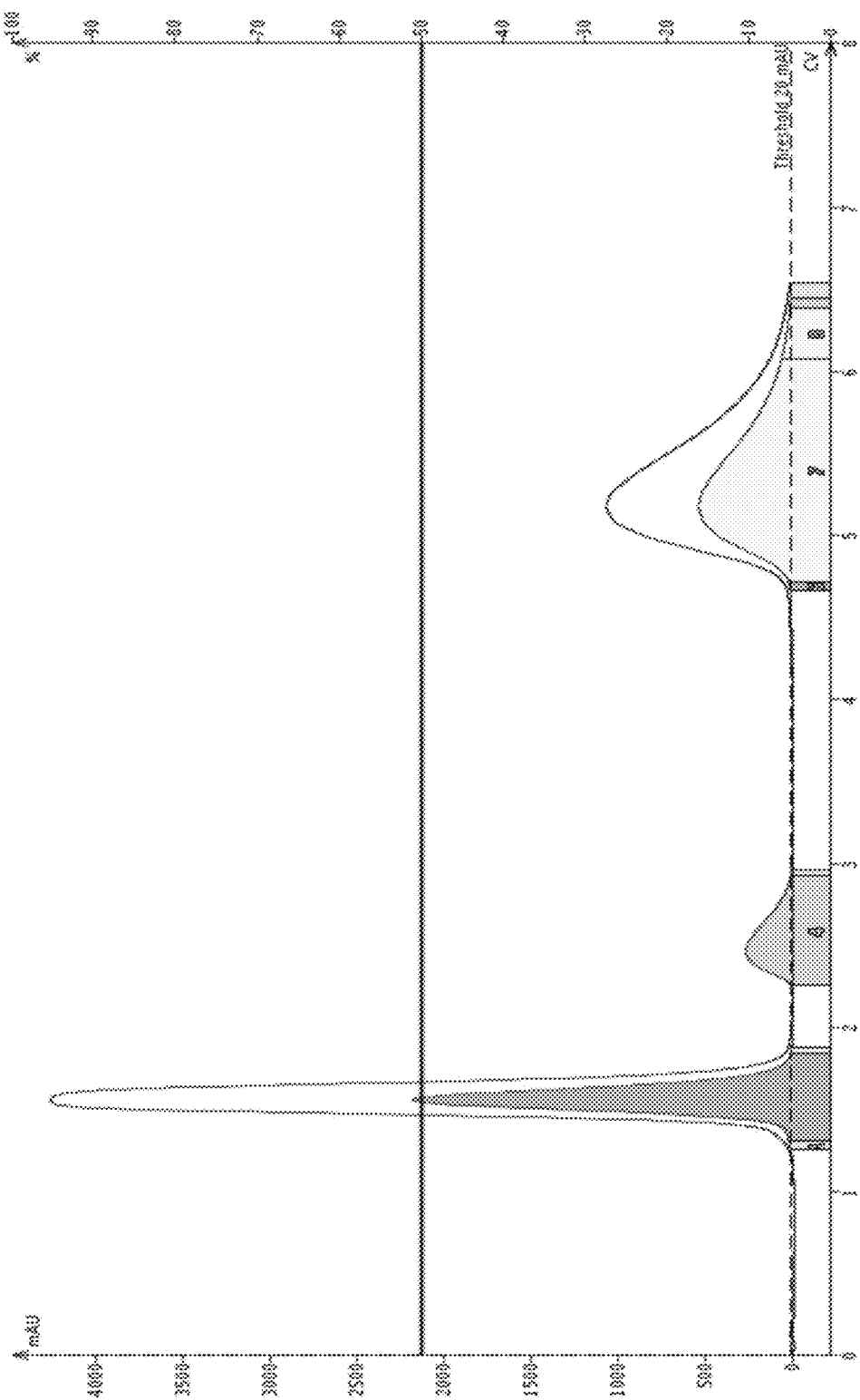
Figure 1(a) – Isocratic equilibration at a default flow rate of 25ml/min

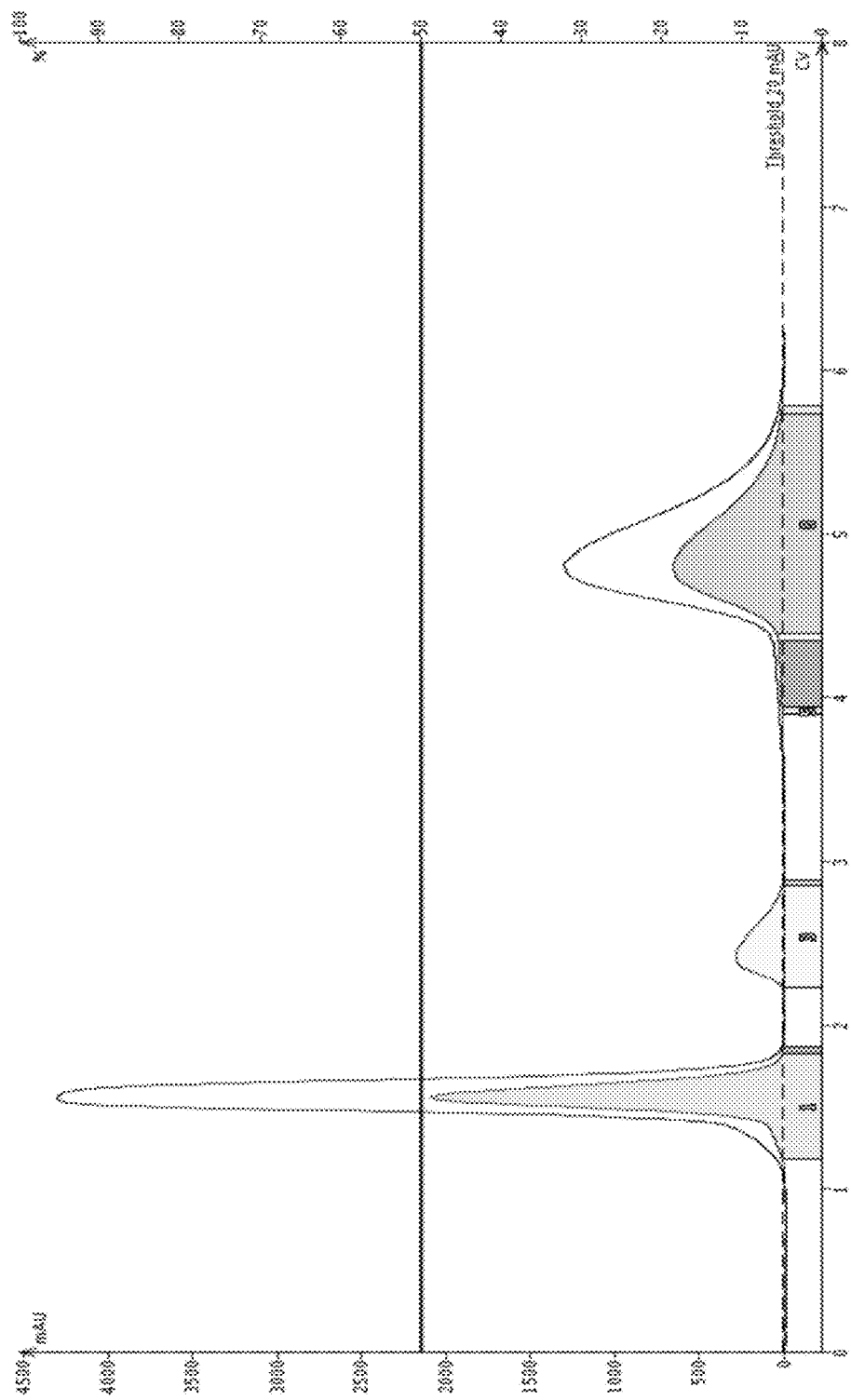
Figure 1(b) – Gradient equilibration at 200ml/minute

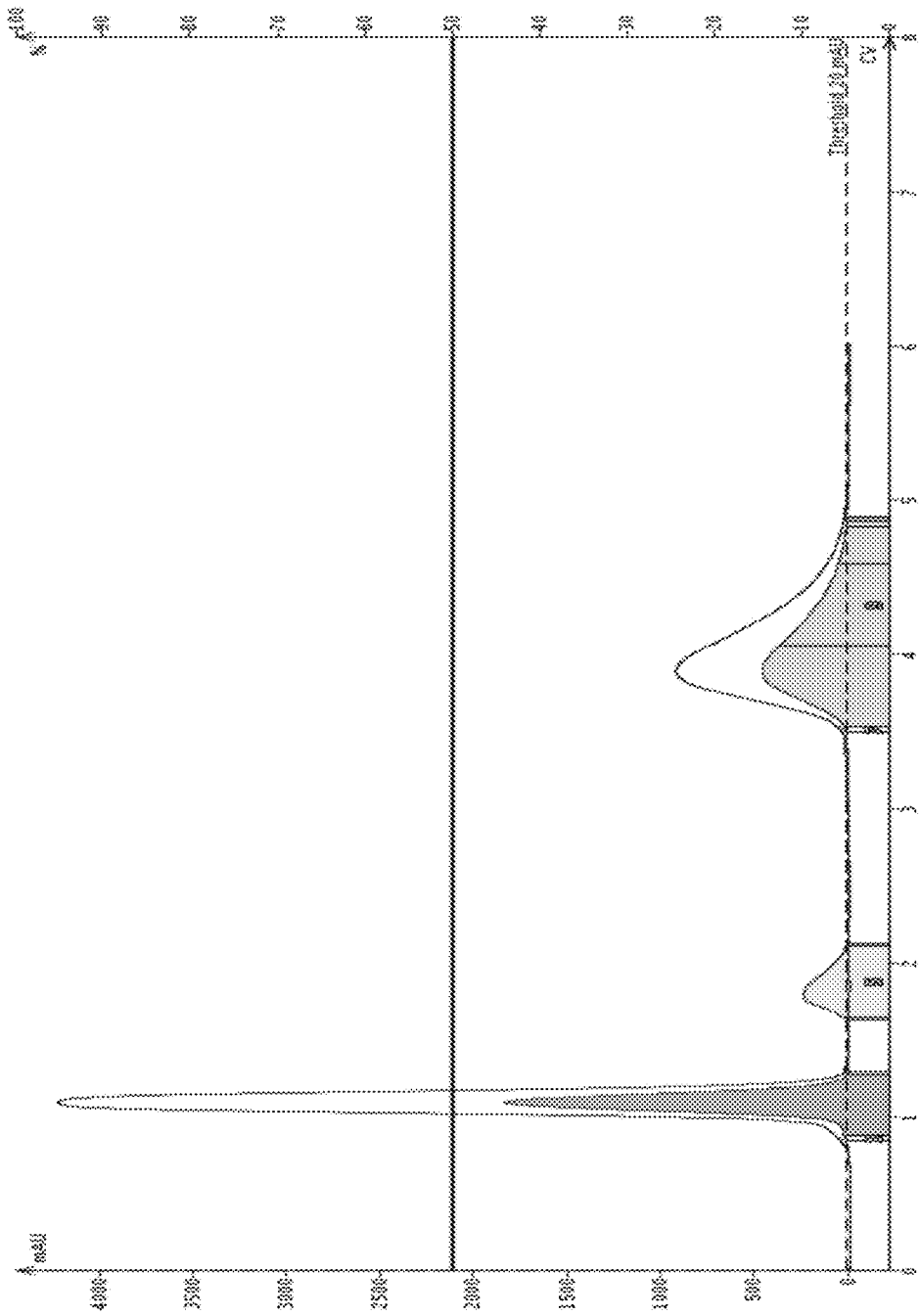

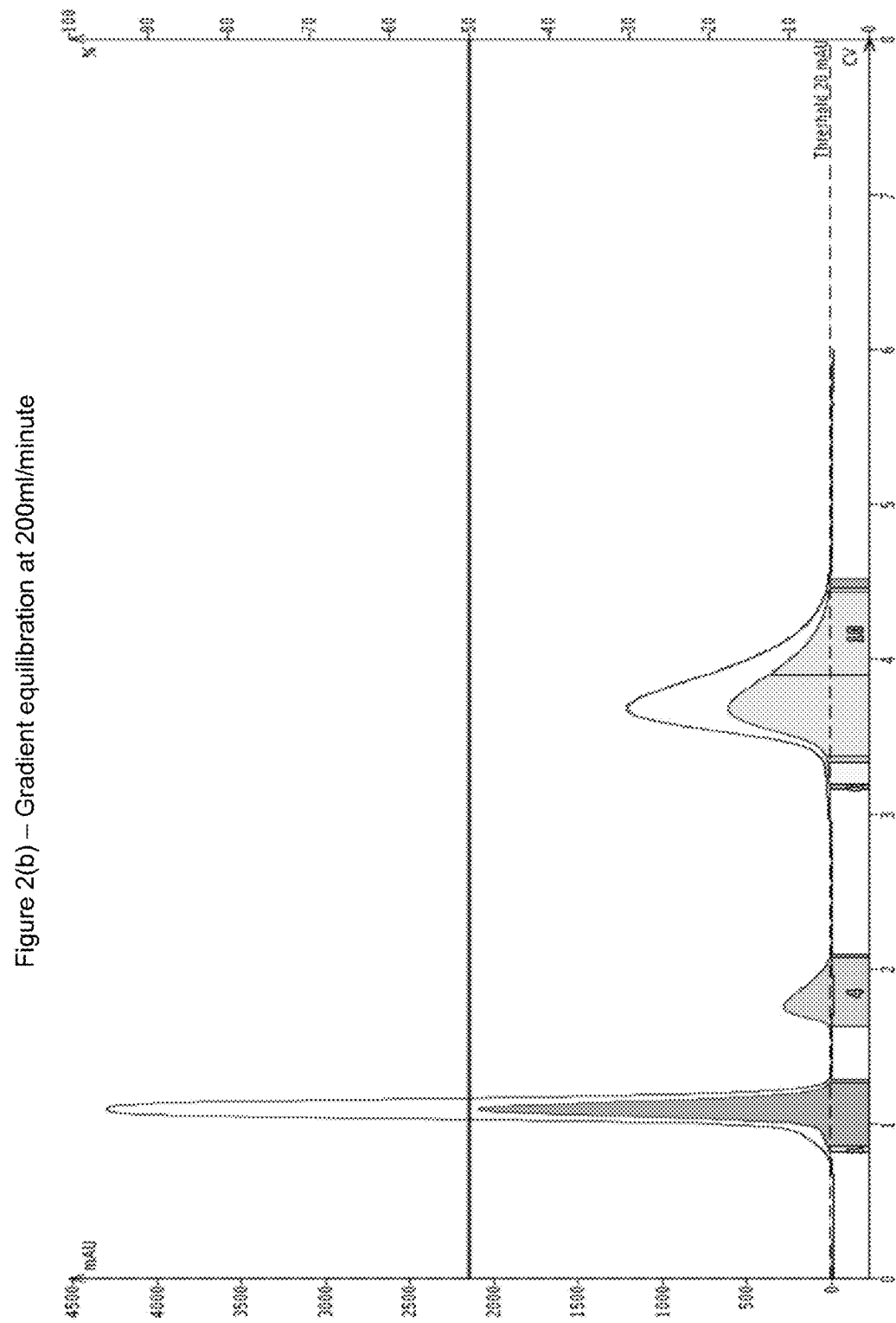
Figure 2(b) — Gradient equilibration at 200ml/minute

METHOD AND APPARATUS FOR THE EQUILIBRATION OF A PACKED CHROMATOGRAPHY COLUMN

TECHNICAL FIELD

The present invention relates to liquid chromatography and more specifically to flash chromatography where high pressure is used to force a liquid through the chromatography column.

BACKGROUND

High pressure chromatography (HPLC) is a well-known chromatography mode wherein a pressurized liquid is used to force a sample through a chromatography column packed with a suitable particle media, known as the stationary phase. Flash chromatography differs from preparative HPLC in that larger particles are used to enable fast applications, typical particle sizes being in the broad range of 20-60 um. The Columns may be relatively simple tubes or syringes made from various materials, such as glass, quartz or stainless steel. Polymeric materials are becoming frequently used in pre-packed columns for construction of the columns or frits provided at each end to prevent the media from leaving.

Before running a chrothatographic separation, uniform conditions should be ensured throughout the packing of the column. This is usually provided by running a suitable mobile phase such as a solvent or a buffer through the column, which process is known as the equilibration or conditioning of a packed column. Since flash chromatography is primarily used for fast applications, the equilibration step is advantageously performed as quickly as possible, e.g. by utilizing few column volumes of mobile phase and/or high flow rates.

Grivel et al. (In J Chromatogr A 2010 Jan. 22; 1217(4): 459-72: "Selection of suitable operating conditions to minimize the gradient equilibration time in the separation of drugs by Ultra-High-Pressure Liquid Chromatography with volatile (mass spectrometry-compatible) buffers) relates to reversed phase chromatography. More specifically, this article has recognized that problems are associated with long equilibraticm times in flash chromatography, and presents a study of temperature variation, different flow rates and various additives to the mobile phase used for equilibration. While drawing certain conclusions regarding retention variability and specific equilibration additives, it is also concluded by the authors that the mechanisms which govern equilibration remain very complex and require much further work.

U.S. Pat. No. 6,601,439 ("Method of reducing baseline instabilities in liquid chromatography measurements and liquid chromatography apparatus") relates to high performance chromatography (HPLC) and problems associated by baseline variations, and specifically to instabilities in connection with amino functionalised stationary phases. The '439 patent describes how baseline variations originating from variations in the adsorption of water to the stationary phase have been found to be related to temperature fluctuations. According to this patent, the problems are reduced by the coupling of an additional solid body or liquid bath having high heat capacity and heat conductance to the column to enclose the equipment.

SUMMARY OF THE INVENTION

The present invention relates to the equilibration of chromatography columns, and specifically to problems arising when flow rates are increased. For example, it has been found that during the equilibration of porous particle packings exhibiting large available surface areas, the heat generated by the exothermic reactions involved in the equilibration may impair polyethylene fits of chromatography columns.

The present inventors have found a way to manage and/or control the heat generated during the exothermic reactions commonly involved in the equilibration of the column packing, whereby high flow rates may be utilized without any negative impact on the packing or column integrity.

Thus, the present invention relates to new findings that enable speeding up of a total sample processing time in e.g. in flash chromatography. This may be achieved by using a combination of solvents in a gradient equilibration step.

In a first aspect, the invention relates to a method for equilibrating a chromatography column comprising the steps of (i) providing a packed chromatography column; and (ii) passing a pressurized mobile phase through said column; wherein the mobile phase is obtained by combining at least two liquids, the proportions of which are varied as the mobile phase is passed through the column.

In one embodiment, the variation of said at least two liquids is achieved by combining an increasing proportion of one liquid and a decreasing proportion of another liquid to provide a linear gradient in the mobile phase as it passes the column.

In one embodiment, at least one of the liquids is an organic solvent, such as ethyl acetate and/or hexane.

In one embodiment, the column used in the present method is packed with an inorganic material, such as silica.

In an advantageous embodiment, the mobile phase is passed through the column according to the invention at a flow rate in the range of 50-200 ml/min.

In an advantageous embodiment, the surface area of the packing available to the mobile phase is at least 500 $m^2/g$ dry weight.

However, as the skilled person will appreciate, the gist of the present invention is to use a gradient, rather than isocratic equilibration, if there is a risk of undesired effects to the equipment caused e.g. by heat damaging the fits of a column. Such an effect may appear e.g. for other combinations of (i) exposed surface area and (ii) flow rate than the examples above, in which case the present invention may also be applied. Put differently, the present invention is a method for using gradient equilibration to control the generated heat and maintain it below an acceptable threshold.

In one embodiment, the column and/or the column frits used in the present method are made of a polymeric material, such as polypropylene. In an alternative embodiment, the fits are made from polyethylene.

In a second aspect, the invention relates to a method of controlling the heat generated during the equilibration of a packed chromatography column; wherein the size and material of the column as well as the packing surface area available to the mobile phase are used as parameters to define an equilibration gradient.

In an advantageous embodiment, the packed chromatography column is a flash chromatography column.

In a third aspect, the invention relates to a computer program performing the method according to the invention.

In a fourth aspect, the invention relates to a chromatography system comprising at least one packed chromatography column; vessels for samples and reagents; and tubing to pass one or more liquids between vessel(s) and column(s). Thus, the system according to the invention is capable of controlling the heat generated using the method according to the invention which is described in mine detail above as well as in the detailed description below.

In one embodiment, the system according to the invention further comprises equipment for analysis of one or more target substances separated from other components of a sample in the chromatography column, preferably equipment for mass detection (MS), such as a mass detector. In an alternative embodiment, the detector is an ELSD or UV detector. The system may advantageously be automated.

Further embodiments, combinations of the embodiments and examples of the invention will appear from the detailed description below.

Definitions

The term "equilibration" is used herein as conventionally used in this field, e.g. for the process of achieving a point where pH, conductivity and UV, measured at the column outlet, are identical to the respective values of the applied buffer.

BRIEF DESCRIPTION OF THE DRAWINGS

FIG. 1(a) shows an isocratic equilibration of SNAP Ultra 25 g cartridges (Biotage) at 50:50 v/v Heptane:Ethyl Acetate (%); 1% load; 3 component mixture; at a default flow rate of 25 ml/min.

FIG. 1(b) shows a gradient equilibration according to the invention, as described in Example 1, again using SNAP Ultra 25 g cartridges (Biotage), at 50% Ethyl Acetate % 1% load 3 component mixture at a flow rate of 200 ml/minute.

FIG. 2(a) shows an isocratic equilibration of SNAP Ultra 50 g (Biotage), at 50:50 v/v Heptane:Ethyl Acetate % 1% load 3 component mixture at a default flow rate of 50 ml/min. The equilibration time was 8.05 minutes.

FIG. 2(b) shows a gradient equilibration according to the invention, as described in example 1, again using SNAP Ultra 50 g (Biotage), at 50% Ethyl Acetate %. 1% load 3 comp mix at a flow rate of 200 ml/minutes.

DETAILED DESCRIPTION OF THE INVENTION

In the first aspect of the invention, a method is provided for equilibrating a chromatography column comprising the steps of (i) providing a packed chromatography column; and (ii) passing a pressurized mobile phase through said column; wherein the mobile phase is obtained by combining at least two liquids, the proportions of which are varied as the mobile phase is passed through the column.

In an advantageous embodiment, the variation of said at least two liquids is achieved by combining an increasing proportion of one liquid and a decreasing proportion of another liquid to provide a linear gradient in the mobile phase as it passes the column. The present inventors have found that a linear gradient may be adjusted to maintain an acceptable heat generation even at the more preferred, higher flow rates which without the gradient would impair or even destroy or degrade elements of the hardware such as frits made from polymeric materials.

Equipment and methodologies for providing gradients of mobile phases are commercially available for the elution step, and components such as reagent vessels, pumps and tubing can easily be set up and adjusted by the skilled person to provide an equilibration gradient according to the invention.

As the skilled person will appreciate, the mobile phase may differ in composition depending on the target substance of the sample to be purified; the chromatography packing used; the mode of adsorption of target substance to the packing etc. and may include any multi-solvent system in which the various solvent components are miscible over at least the concentration ranges that will be used for the subsequent separation. In one embodiment, the liquids used are solvents selected from the group consisting of methanol, ethanol, 2-propanol, acetonitrile, ethyl acetate, tetrahydrofuran, acetone, dichloromethane, chloroform, diethyl ether, toluene and hexane. While in most instances a suitable binary liquid system would be expected to provide satisfactory results, as will be appreciated by those skilled in the art, the method according to the invention may be adapted to include more than two liquids. Regardless of how many liquids are incorporated into the mobile phase, the relative concentrations of the liquids used to form the mobile phase should be selected to ensure that the heat generated by the equilibration performed will not exceed a value where negative impact on the hardware used is reached.

Thus, in one embodiment, at least one of the liquids is an organic solvent, such as ethyl acetate and/or hexane. In an advantageous embodiment, the equilibration is started with 0% of a first liquid, such as ethyl acetate, and 100% of a second liquid, such as hexane. The ethyl acetate proportion is then increased in the mobile phase with the corresponding decrease in the hexane proportion until a composition equivalent to the solvent composition of the sample to be run is reached. The increase may be stepped or linear, in an advantageous embodiment, the gradient is linear.

As discussed above, the present invention enables utilizing flow rates during the equilibration which without the use of a gradient would damage packing and/or hardware due to the heat generation. Thus, in one embodiment, the mobile phase is passed through the column at a flow rate of up to 200 ml/min, such as a flow rate in the range of 50-100 ml/min. The skilled person will easily be able to determine the highest possible flow rate, or optimal flow rate, by simple testing.

The chromatography column according to the invention may be packed with any commonly used chromatography media, sometimes denoted adsorption material. A typical column for flash chromatography may be a cartridge having a diameter of about 1-20 cm. In an advantageous embodiment, the column is packed with an inorganic media, such as silica, silica gel, alumina or diatomeous earth. Silica packed cartridges e.g. for flash chromatography are commercially available e.g. from Biotage.

In one embodiment of the present method, the surface area of the packing available to the mobile phase is at least 500 $m^2/g$ (dry weight). An example of a suitable packing is KP-Sil (Biotage), which is irregular silica with a standard surface area of 500 $m^2/g$. In a specific embodiment, the surface area available to the mobile phase is at least 700 $m^2/g$, such as in the range of 700-800 $m^2/g$. An illustrative example of a chromatography media advantageously used with the method according to the invention is the packing of Biotage SNAP ULTRA flash cartridges. With a surface area of 700 $m^2/g$.

The column and other hardware used may be of any commonly used material, such as polymeric materials which present certain heat sensitivity if temperatures are raised beyond the standard values. Thus, in one embodiment, the column and/or the column frits are made of polymeric material, such as polypropylene or polyethylene, wherein at least one element is made of a material having limited heat sensitivity. The column used is often a cartridge prepacked with silica particles, such as Biotage SNAP ULTRA.

In the second aspect of the invention, a method is provided for controlling and/or avoiding excess of heat generated during the equilibration of a packed chromatography column. In the present method, the size and material of the column as well as the particle size and available surface area of the packing are used as parameters to define a liquid gradient suitable for an intended equilibration. By using the present method, a flow rate is determined which enables the most efficient flow rates possible in an equilibration process without exceeding a predetermined temperature in packing and/or hardware. Thus, this aspect of the invention may be used to design the optimal or most suitable processing conditions that enable a fast equilibration and hence decrease the total processing time of a certain chromatography process.

In the third aspect of the invention, a computer program is provided which is capable of performing the method according to the invention.

In a fourth aspect, the invention provides a chromatography system comprising at least one packed chromatography column; vessels for samples and reagents; and tubing to pass one or more liquids between vessel(s) and column(s); which system is capable of controlling the heat generated by the exothermic reactions taking place during equilibration. The present system is advantageously used with a method according to the first aspect of to the invention.

In one embodiment, the system according to the invention further comprises equipment for analysis of one or more target substances separated from other components of a sample in the chromatography column, preferably equipment for mass detection (MS), such as a mass detector. In alternative embodiments, the detector is an UV/VIS detector, a flame ionization detector, infrared detector or any other detector suitable to combine with flash chromatography. The system may advantageously be automated. In one embodiment, the system according to the invention is a flash chromatography system, which enables intelligent sampling by providing the mass detector with an appropriate amount of material from the flash run. In one embodiment, the system automatically adjusts to changes in flash flow rate when different types or sizes of cartridges are used. Thanks to the optimized equilibration according to the invention, such a system provides a faster separation of samples for purification.

Experimental

The present examples are provided for illustrative purposes only, and should not be construed as limiting the present invention in any way. All references included below or elsewhere in the present application are hereby included by reference.

Materials and Methods

SNAP/ZIP Gradient Equilibration and PD0170 Isolera High Performance Upgrade were used below. The abbreviation "CV" will be used below to denote 'column volume', as used widely in the field of chromatography.

The aim of the examples was to determine the feasibility of employing a gradient equilibration as a means of negating the effect of 'heat of hydration' when equilibrating SNAP ultra columns in 10 g to 340 g and ZIP Sphere columns in the 5 g-120 g format range when using isocratic mobile phases containing 30% and 50% Ethyl Acetate at high flow rates (greater than default).

Experimental

Evaluations were carried out in standard SNAP & SNAP Ultra 340 g, 100 g, 50 g, 25 g and 10 g columns (Biotage)

ZIP & ZIP Sphere formats 10 g, 30 g, 45 g, 80 g, 120 g.

Max flow rate data for all formats for flow rate reference

Each configuration was equilibrated to a final solvent combination of Heptane:Ethyl Acetate 70:30 v/v and 50:50 mobile phase at elevated flow rates.

Results: Feasibility

All evaluations were constructed to encompass a CV equilibration range of 3-5 CV on each selected column range.

| A: Heptane B: Ethyl Acetate % | CV |
|---|---|
| Gradient 1 | |
| A to B - 10 to 30 | 2 |
| Hold 30 | 2 |
| Gradient 2 | |
| A to B - 10 to 30 | 2.5 |
| Hold 30 | 2 |
| Gradient 3 | |
| 10 | 1 |
| 10-50 | 2 |
| Hold 50 | 2 |

Flow rate table update ZIP, SNAP, ZIP Sphere, SNAP Ultra, all available standard sizes. Based on unmodified default equilibration guidelines and 340 g sizes, using standard Ethyl Acetate concentration of 7%.

N=5 for each format. Averaged result.

Flow rate gradually increased to a max. Flow just below the safe registered pressure limit for each format type. Max flow also dictated by the processing system in this case Isolera one 200 ml/min Backpressure registered for each max flow

TABLE 1

| Format | Media | Default Flow ml/min | Bed Mass (g) | Max. Flow rate ml/min | Back-pressure (bar) | Column Pressure Rating (bar) |
|---|---|---|---|---|---|---|
| ZIP | KPSil | 6 | 5 | 200 | 6.0 | 10 |
| ZIP | Sphere | 6 | 5 | 170 | 6.8 | 7 |
| SNAP | KPSil | 12 | 10 | 200 | 4.7 | 7 |
| SNAP | Ultra | 12 | 10 | 165 | 6.9 | 7 |
| ZIP | KPSil | 12 | 10 | 200 | 6.0 | 10 |
| ZIP | Sphere | 12 | 10 | 200 | 6.9 | 7 |

TABLE 2

| Format | Media | Default Flow ml/mm | Bed Mass (g) | Max. Flow rate ml/min | Backpressure (bar) | Column Pressure Rating (bar) |
|---|---|---|---|---|---|---|
| SNAP | KPSil | 25 | 25 | 200 | 4.2 | 7 |
| SNAP | Ultra | 25 | 25 | 200 | 6.7 | 7 |
| ZIP | KPSil | 20 | 30 | 200 | 5.4 | 10 |
| ZIP | Sphere | 20 | 30 | 200 | 5.6 | 7 |

TABLE 3

| Format | Media | Default Flow ml/min | Bed Mass (g) | Max. Flow rate ml/min | Backpressure (bar) | Column Pressure Rating (bar) |
|---|---|---|---|---|---|---|
| SNAP | KPSil | 50 | 50 | 200 | 3.5 | 7 |
| SNAP | Ultra | 50 | 50 | 200 | 5.5 | 7 |
| ZIP | KPSil | 30 | 45 | 200 | 4.9 | 10 |
| ZIP | Sphere | 30 | 45 | 200 | 5.0 | 7 |

TABLE 4

| Format | Media | Default Flow ml/min | Bed Mass (g) | Max. Flow rate ml/min | Backpressure (bar) | Column Pressure Rating (bar) |
|---|---|---|---|---|---|---|
| ZIP | KPSil | 50 | 80 | 200 | 4.2 | 8 |
| ZIP | Sphere | 50 | 80 | 200 | 4.1 | 7 |
| SNAP | KPSil | 50 | 100 | 200 | 4.5 | 7 |
| SNAP | Ultra | 50 | 100 | 170 | 6.8 | 7 |
| ZIP | KPSil | 50 | 120 | 200 | 4.6 | 10 |
| ZIP | Sphere | 50 | 120 | 200 | 4.8 | 7 |

TABLE 5

| Format | Media | Default Flow ml/min | Bed Mass (g) | Max. Flow rate ml/min | Back-pressure (bar) | Column Pressure Rating (bar) |
|---|---|---|---|---|---|---|
| SNAP | KPSil | 100 | 340 | 200 | 3.0 | 5 |
| SNAP | Ultra | 100 | 340 | 200 | 4.4 | 5 |

TABLE 6

| Format | Media | Default Flow ml/min | Bed Mass (g) | Max. Flow rate ml/min | Back-pressure (bar) | Column Pressure Rating (bar) |
|---|---|---|---|---|---|---|
| SNAP | KPSil | 100 | 340 | 500 | 2.8 | 5 |
| SNAP | Ultra | 100 | 340 | 450 | 4.4 | 5 |

The gradient equilibration development according to the invention was based on some precursory evaluations that indicated the use of gradients to eliminate the intense heat of hydration experienced with all formats utilising high ethyl acetate concentrations at high flow rates.

Example 1—Equilibration According to the Invention

The gradient used for equilibration according to the invention was 50% Ethyl Acetate Concentration:
10-10% 1 CV,
10-50% 2 CV,
Hold 50% 2 CV.

From Table 1 below, it can be concluded that a gradient according to the invention allows the conditioning of all formats at maximum determined flow rates at 50% Ethyl Acetate although the volume for equilibration has increased the equlibration time vs Isocratic has decreased by approx 75%.

The table also compares the time taken to condition the same formats with a lower % of ethyl acetate (7%) using the default flow rates for the formats using the Biotage Isolera system. The lower % isocratic equilibration data was used as a comparison as the heat of hydration would be at its worst at 50% ethyl acetate under normal isocratic conditions. The flow rates used were the maximum attainable and safe flow rates determined earlier for each format, as this represents the worst case scenario i.e. the highest flow and very high ethyl acetate concentration for equilibration.

TABLE 7

Results of Example 1

| Format | Equilibration Flow rate ml/min | Gradient number | Backpressure (Bar) | Equilibration Time (mins) | Default Flow (ml/min) | Isocratic Equilibration Time (default) |
|---|---|---|---|---|---|---|
| 10 g SNAP Ultra | 165 | 3 | 6.5 | 0.51 | 12 | 7.08 |
| 25 g SNAP Ultra | 200 | 3 | 6.8 | 1.12 | 25 | 9.0 |
| 50 g SNAP Ultra | 200 | 3 | 5.5 | 2.07 | 50 | 8.5 |
| 100 g SNAP Ultra | 170 | 3 | 6.4 | 4.52 | 50 | 16.4 |
| 340 g SNAP Ultra | 200 | 3 | 5.4 | 14.55 | 100 | 29.1 |
| 5 g Zip Sphere | 170 | 3 | 6:4 | 0.12 | 6 | 6.6 |
| 10 g Zip Sphere | 200 | 3 | 6.5 | 0.21 | 12 | 6.5 |
| 30 g Zip Sphere | 200 | 3 | 5.4 | 1.04 | 20 | 11.2 |
| 45 g ZIP Sphere | 200 | 3 | 4.9 | 1.20 | 30 | 10 |
| 80 g ZIP Sphere | 200 | 3 | 4.4 | 2.32 | 50 | 10 |
| 120 g ZIP Sphere | 200 | 3 | 5.0 | 3.35 | 50 | 17 |
| 10 g SNAP KPSil | 200 | 3 | 5.0 | 0.22 | 12 | 6.25 |
| 25 g SNAP KPSil | 200 | 3 | 4.7 | 047 | 25 | 6.6 |
| 50 g SNAP KPSil | 200 | 3 | 3.8 | 1.37 | 50. | 6.6 |
| 100 g SNAP KPSil | 170 | 3 | 4.4 | 3.17 | 50 | 13.2 |
| 340 g SNAP KPSil | 200 | 3 | 3.2 | 12.75 | 100 | 25.5 |
| 5 g Zip KPSil | 170 | 3 | 6.1 | 0.14 | 6 | 6.6 |
| 10 g Zip KPSil | 200 | 3 | 6.8 | 0.22 | 12 | 6.25 |
| 30 g Zip KPSil | 200 | 3 | 5.9 | 1.07 | 20 | 11.25 |
| 45 g ZIP KPSil | 200 | 3 | 4.9 | 1..5 | 30 | 10 |
| 80 g ZIP KPSil | 200 | 3 | 4.4 | 2.32 | 50 | 10.2 |
| 120 g ZIP KPSil | 200 | 3 | 4.3 | 4.14 | 50 | 17 |

Example 2—Comparative

The aim of this example was to investigate the effect on conditioning the column at default flow rate using 70/30 Heptane/EtOAc.

SNAP ULTRA N=5 Columns tested; 10 g; 25 g; 50 g; 100 g and 340 g.

10 g—default flow rate 12 ml/min 25 g—default flow rate 25 ml/min 50 g—default flow rate 50 ml/min 100 g—default flow rate 50 ml/min 340 g—default flow rate 100 ml/min The results are presented in the Tables below:

TABLE 8

Isocratic run

| 340 g Column | Flow rate | Observation | Over pressured |
|---|---|---|---|
| 1 - 70/30 Heptane/EtOAc | 100 ml/min | 782 ml before over pressured | Yes |
| 2 - 70/30 Heptane/EtOAc | 100 ml/min | 767 ml before over pressured | Yes |
| 3 - 70/30 Heptane/EtOAc | 100 ml/min | 770 ml before over pressured | Yes |
| 4 - 70/30 Heptane/EtOAc | 50 ml/min | Conditioned by 2 column volumes with max. Pressure 0.8 bar. After 3 column volumes flow increased to 100 ml/min pressure 1.7 bars. 150 ml/min 3 bar. 200 ml/min 4.2 bar | No |
| 5 - 80/20 Heptane/EtOAc | 100 ml/min | Conditioned with maximum pressure 2.1 bar. | No |

TABLE 9

| 100 g Column | Flow rate | Observation | Over pressured |
|---|---|---|---|
| 1 | 50 ml/min | Conditioned with maximum pressure 1.5 bar | No |
| 2 | 50 ml/min | Conditioned with maximum pressure 1.5 bar | No |
| 3 | 50 ml/min | Conditioned with maximum pressure 1.5 bar | No |
| 4 | 50 ml/min | Conditioned with maximum pressure 1.5 bar | No |
| 5 | 50 ml/min | Conditioned with maximum pressure 1.5 bar | No |

TABLE 10

| 50 g Column | Flow rate | Observation | Over pressured |
|---|---|---|---|
| 1 | 50 ml/min | Conditioned with maximum pressure 1.4 bar | No |
| 2 | 50 ml/min | Conditioned with maximum pressure 1.4 bar | No |
| 3 | 50 ml/min | Conditioned with maximum pressure 1.1 bar | No |
| 4 | 50 ml/min | Conditioned with maximum pressure 1.2 bar | No |

TABLE 11

| 25 g Column | Flow rate | Observation | Over pressured |
|---|---|---|---|
| 1 | 25 ml/min | Conditioned with maximum pressure 0.7 bar | No |
| 2 | 25 ml/min | Conditioned with maximum pressure 0.6 bar | No |
| 3 | 25 ml/min | Conditioned with maximum pressure 0.8 bar | No |
| 4 | 25 ml/min | Conditioned with maximum pressure 0.8 bar | No |
| 5 | 25 ml/min | Conditioned with maximum pressure 0.8 bar | No |

TABLE 12

| 10 g Column | Flow rate | Observation | Over pressured |
|---|---|---|---|
| 1 | 12 ml/min | Conditioned with maximum pressure 0.4 bar | No |
| 2 | 12 ml/min | Conditioned with maximum pressure 0.3 bar | No |
| 3 | 12 ml/min | Conditioned with maximum pressure 0.4 bar | No |
| 4 | 12 ml/min | Conditioned with maximum pressure 0.4 bar | No |
| 5 | 12 ml/min | Conditioned with maximum pressure 0.4 bar | No |

This example highlights the fit melting problem of the prior art equilibration methods. In this experiment, the SNAP Ultra 340 g column was the main cause for concern as it could not be conditioned at default low flow rate (100 ml/min). The present invention now shows that columns may successfully be equilibrated at higher flow rates, which in the prior art was possible only at lower ethyl acetate concentrations such as 10% ethyl acetate or less, but not at the higher flow rates due to the heat generation and the frit softening.

Thus, the use of a gradient for equilibration according to the invention enables an increase in the flow rate including equilibration to three times the present default for columns up to 50 g and twice default for columns greater than 50 g (inc. 340 g).

The invention claimed is:

1. A method for equilibrating a chromatography column, comprising:
   (i) providing a packed chromatography column; and
   (ii) passing a pressurized mobile phase through said column;
   wherein the size and material of the column as well as the packing surface area available to the mobile phase are used as parameters to define an equilibration gradient comprised of two liquids, the proportions of which are varied as the mobile phase is passed through the column, whereby an optimal flow rate is provided without exceeding a predetermined temperature and the heat generated during the equilibration of a packed chromatography column is controlled.

2. The method according to claim 1, wherein the packed chromatography column is a flash chromatography column.

3. The method according to claim 1, which has been automated.

4. The method according to claim 1, wherein at least one of the liquids is an organic solvent.

5. The method according to claim 4, wherein the organic solvent comprises ethyl acetate.

6. The method according to claim 4, wherein the organic solvent comprises hexane.

7. The method according to claim 1, wherein the column is packed with a media.

8. The method according to claim 7, wherein the media is silica.

9. The method according to claim 1, wherein at least one of the column and the column frits is made of a polymeric material.

10. The method according to claim 9, wherein the polymeric material is polypropylene.

11. The method according to claim 9, wherein the polymeric material is polyethylene.

12. A chromatography system comprising at least one packed chromatography column and a computer program for performing the method according to claim 1; vessels for samples and reagents; and tubing to pass one or more liquids between vessel(s) and column(s).

13. The system according to claim 12, which comprises equipment for analysis of one or more target substances separated from other components of a sample in the chromatography column.

14. The system according to claim 12, wherein the equipment is for mass detection.

\* \* \* \* \*